United States Patent
Liu et al.

(10) Patent No.: US 12,257,094 B2
(45) Date of Patent: Mar. 25, 2025

(54) METHOD FOR OBTAINING BRAIN PERFUSION PARAMETER MAPS THROUGH COMPUTED TOMOGRAPHY PERFUSION IMAGING AND ITS SYSTEM

(71) Applicant: ArteryFlow Technology Co., Ltd., Zhejiang (CN)

(72) Inventors: Xin Liu, Zhejiang (CN); Jingsong He, Zhejiang (CN); Wenfei Shi, Zhejiang (CN); Xiaochang Leng, Zhejiang (CN); Jianping Xiang, Zhejiang (CN)

(73) Assignee: ArteryFlow Technology Co., Ltd., Hangzhou (CN)

( * ) Notice: Subject to any disclaimer, the term of this patent is extended or adjusted under 35 U.S.C. 154(b) by 327 days.

(21) Appl. No.: 17/891,864

(22) Filed: Aug. 19, 2022

(65) Prior Publication Data

US 2023/0054153 A1 Feb. 23, 2023

(30) Foreign Application Priority Data

Aug. 20, 2021 (CN) .......................... 202110962392.X (51) Int. Cl.
*A61B 6/50* (2024.01)
*A61B 6/00* (2006.01)

(52) U.S. Cl.
CPC .............. *A61B 6/507* (2013.01); *A61B 6/481* (2013.01)

(58) Field of Classification Search
CPC ................................. A61B 6/507; A61B 6/481
See application file for complete search history.

(56) References Cited

U.S. PATENT DOCUMENTS

2005/0113680 A1* 5/2005 Ikeda .................... G06T 7/0012
128/920

* cited by examiner

*Primary Examiner* — Sam Bhattacharya (57) ABSTRACT

The application discloses a method, a device, a system and a computer storage medium for obtaining the CT perfusion imaging parameter maps of brain. The method includes: obtaining CT perfusion images, pre-processing the CT perfusion images, and obtaining discrete contrast agent concentration curve C(n) of each pixel point in the brain tissue; reading the acquisition time information of the CT perfusion images to obtain the acquisition time array T(n); intercepting the acquisition time array T(n) to obtain the relative acquisition time array t(n); combining the discrete contrast agent concentration curve C(n) with the corresponding relative acquisition time array t(n) to obtain the discrete time-concentration curve $C(t_n)$ of each pixel point in the brain tissue; after fitting or interpolating the discrete time-concentration curve $C(t_n)$, re-discretizing at the same time interval, and obtaining the discrete time-concentration curve C(n)' of each pixel point in brain tissue. The same processing is performed on the arterial input change curve AIF(n) and the venous output change curve VOF(n). The application improves the usability of the tissue density time curve, which helps to reduce the difficulty of solving and improve the accuracy of solving.

19 Claims, 5 Drawing Sheets

METHOD FOR OBTAINING BRAIN PERFUSION PARAMETER MAPS THROUGH COMPUTED TOMOGRAPHY PERFUSION IMAGING AND ITS SYSTEM

CROSS-REFERENCE TO RELATED APPLICATION

This application claims priority from the Chinese patent application 202110962392X filed Aug. 20, 2021, the content of which is incorporated herein in the entirety by reference.

TECHNICAL FIELD

The present disclosure relates to the technical fields of image processing and medical engineering, and in particular, to a method, device, system and computer storage medium for obtaining CT perfusion imaging parameter maps of brain.

BACKGROUND

Stroke is an acute cerebrovascular disease, which is a group of diseases that cause brain damage due to the sudden rupture of blood vessels in the brain or the inability of blood to flow into the brain due to vascular blockage, including ischemic and hemorrhagic strokes. This disease has very high disability rate and high fatality rate. Changes in the structure of human life have led to an increasing incidence of acute ischemic stroke. In recent years, stroke has become one of the leading causes of death in our country. In 2018, the stroke mortality rate in China was 149.49/100,000, accounting for 22.3% of the total mortality rate of Chinese residents. Among them, acute ischemic stroke (cerebral infarction) is the most common type of stroke, accounting for 60%~80% of all strokes.

Perfusion imaging is most widely used in acute stroke and oncology. In stroke diagnosis, the purpose of perfusion imaging is to determine the extent of diseased tissue and to delineate ischemic tissue that can be re-perfused. Perfusion measurements are increasingly used for assessment, staging, and post-treatment monitoring.

Cerebral CT perfusion imaging (CTP) is an imaging technique for evaluating cerebral parenchymal blood perfusion, and it is also an important imaging method for detecting acute ischemic stroke. This technique involves rapid sequential CT scans of the head following an intravenous injection of contrast agent, such as iodinated contrast. Based on the tracer kinetic model and tracer dilution theory, the acquired contrast-enhanced and time-resolved CT images are processed by deconvolution-based or non-deconvolution-based algorithms to generate perfusion parameter maps such as cerebral blood volume (CBV), cerebral blood flow (CBF), mean transient time (MTT), etc.

In the prior art, during the acquisition of CT perfusion images, images of different frames of the same image sequence may have different acquisition times due to different image acquisition devices or acquisition methods. Currently, the deconvolution method is the most commonly used CT perfusion image processing method, see formula (1): $c(t)=AIF(t)*k(t)$; $C(t)$ is the tissue time density curve; $AIF(t)$ is the arterial input function; $k(t)$ is the residual function. Since images of different frames have different acquisition times, directly using the acquired original images to calculate the residual function $k(t)$ will lead to problems such as decreased accuracy of subsequent perfusion parameter maps, difficulty in solving, and low temporal resolution of the residual function $k(t)$.

SUMMARY

In order to solve the problems of low accuracy of perfusion parameter maps, great difficulty in solving perfusion parameter maps, and low time resolution of residual function $k(t)$ in the prior art, the disclosure provides a method for obtaining CT perfusion imaging parameter maps of brain.

The method for obtaining CT perfusion imaging parameter maps of brain in the disclosure includes:

Obtaining CT perfusion images, pre-processing the CT perfusion images, and obtaining the discrete contrast agent concentration curve $C(n)$ of each pixel point in the brain tissue, where n is the nth acquisition time point, and $C(n)$ is the contrast agent concentration in the tissue corresponding to the nth time point;

Reading the acquisition time information of the CT perfusion images, and obtaining the acquisition time arrays $T(n)$, where n is the nth time point, $T(n)$ is the physical time of the image acquisition device when the nth image was collected, $T(n)$ Include $Tc(n)$ corresponding to discrete tissue density change curve $C(n)$;

Intercepting the acquisition time array $T(n)$ to obtain the relative collection time arrays $t(n)$, where $t(n)$ include $tc(n)$ corresponding to the discrete contrast agent concentration curve $C(n)$;

Combining the discrete contrast agent concentration curve $C(n)$ with the corresponding relative collection time arrays $t(n)$ to obtain the discrete time-concentration curve $C(t_n)$ of each pixel point in the brain tissue; After fitting or interpolating the discrete time-concentration curve $C(t_n)$ of each pixel point, re-discretizing at the same time interval to obtain the discrete time-concentration curve $C(n)'$ of each pixel point in brain tissue, obtaining CT perfusion imaging parameter maps of brain according to the time-concentration curve $C(n)'$.

Optionally, the method further includes: acquiring CT perfusion images, performing pre-processing on the CT perfusion images, and obtaining an arterial input function $AIF(n)$, where n is the nth acquisition time point; Reading the acquisition time information of the CT perfusion images, and obtain the acquisition time arrays $T(n)$, where n is the nth time point, $T(n)$ is the physical time of the image acquisition device when the nth image was collected, $T(n)$ also include $Ta(n)$ corresponding to the arterial input function $AIF(n)$;

Intercepting the acquisition time arrays $T(n)$ to obtain the relative acquisition time arrays $t(n)$, $t(n)$ also include $ta(n)$ corresponding to the arterial input function $AIF(n)$;

Combining the arterial input function $AIF(n)$ with the corresponding relative acquisition time arrays $t(n)$ to obtain the arterial input function $AIF(t_n)$;

After fitting or interpolating the arterial input function $AIF(t_n)$, re-discretizing at the same time interval to obtain the discrete arterial input function $AIF(n)'$, and obtaining the CT perfusion imaging parameter maps of brain according to the arterial input function $AIF(n)'$.

Optionally, the method includes: acquiring CT perfusion images, performing pre-processing on the CT perfusion images, and obtaining discrete contrast agent concentration curve $C(n)$ of each pixel point in the brain tissue and an arterial input function $AIF(n)$, where n is the nth acquisition time point;

Reading the acquisition time information of the CT perfusion images, and obtain the acquisition time arrays $T(n)$, where n is the nth time point, T(n) is the physical time of the image acquisition device when the nth image was collected, T(n) Include Tc (n) and Ta(n) corresponding to the discrete contrast agent concentration curve C(n) and the arterial input function AIF(n), respectively;

Intercepting the acquisition time arrays T(n) to obtain the relative acquisition time arrays t(n), t(n) include tc(n) and ta(n) corresponding to the discrete contrast agent concentration curve C(n) and the arterial input function AIF(n), respectively;

Combining the discrete contrast agent concentration curve C(n) and the arterial input function AIF(n) with the corresponding relative acquisition time arrays t(n) respectively to obtain the arterial input function $AIF(t_n)$ and the discrete time-concentration curve $C(t_n)$ of each pixel point in the brain tissue;

After fitting or interpolating the discrete time-concentration curve $C(t_n)$ of each pixel point and the arterial input function $AIF(t_n)$ respectively, re-discretizing at the same time interval to obtain the discrete time-concentration curve C(n)' and the arterial input function AIF(n)'.

Optionally, the method further includes: According to the formula c(t)=AIF(t)*k(t), the time-concentration curve C(n)' of each pixel point in brain tissue and the arterial input function AIF(n)' are processed to obtain the discrete residual function k(t)';

where t is the time and k(t) is the residual function.

Optionally, the intercepting the acquisition time array T(n) to obtain the relative collection time arrays t(n), which specifically includes:

Finding the minimum value Tmin of the acquisition time array T(n) according to the acquisition time array T(n), processing the acquisition time array T(n) according to Tmin, and obtaining the relative collection time arrays t(n) start from the time Tmin.

Optionally, the intercepting the acquisition time array T(n) to obtain the relative collection time arrays t(n), which specifically includes:

The acquisition time arrays T(n) are converted into the time value measured in seconds, according to the format of the acquisition time in the CT perfusion images;

Traversing the minimum value t(0) of the acquisition time array of each layer of the CT perfusion images, and finding the minimum value Tmin in all the acquisition time arrays T(n);

Subtracting Tmin from each element in the collection time array T(n) of each pixel point to obtain the relative collection time array t(n) of each pixel point start from the time Tmin.

Optionally, the discrete time intervals of the discrete time-concentration curve C(n)' and the arterial input function AIF(n)' are the same, and the discrete time-concentration curve C(n)' and the arterial input function AIF(n)' start at the same time.

Optionally, the method further includes: Acquiring CT perfusion images, performing pre-processing on the CT perfusion images, and obtaining a venous output function VOF(n), where n is the nth acquisition time point; Reading the acquisition time information of the CT perfusion images, and obtaining the acquisition time arrays T(n), where n is the nth time point, T(n) is the physical time of the image acquisition device when the nth image was collected, T(n) also include Tv(n) corresponding to the venous output function VOF(n);

Intercepting the acquisition time arrays T(n) to obtain the relative acquisition time arrays t(n), t(n) also include tv(n) corresponding to the venous output function VOF(n);

Combining the venous output function VOF(n) with the corresponding relative acquisition time arrays t(n) to obtain the venous output function $VOF(t_n)$;

After fitting or interpolating the venous output function $VOF(t_n)$, re-discretizing at the same time interval to obtain the discrete venous output function VOF(n)', and obtaining the CT perfusion imaging parameter maps of brain according to the venous output function VOF(n)';

The discrete time intervals of the discrete time-concentration curve C(n)' and the venous output function VOF(n)' are the same, and the discrete time-concentration curve C(n)' and the venous output function VOF(n)' start at the same time.

Optionally, the pre-processing of the CT perfusion images includes brain tissue extraction.

Optionally, the pre-processing of the CT perfusion images includes motion correction, filtering, segmenting the skull and extract brain area, finding arterial and venous points automatically on the CT perfusion image.

The disclosure also provides a device for CT perfusion imaging parameter maps of brain, comprising:

The pre-processing module acquires the CT perfusion images, performs pre-processing on the CT perfusion images, and obtains pre-processed CT perfusion images of brain, including the discrete contrast agent concentration curve C(n) of each pixel point in brain tissue and the global arterial input function AIF(n) and the venous output function VOF(n);

The time processing module reads the acquisition time information of the CT perfusion images, and obtains the acquisition time arrays T(n), where n is the nth time point, and T(n) is the physical time of the image acquisition device when the nth image is collected, T(n) corresponds to the contrast agent concentration curve C(n); intercepts the acquisition time array T(n) to obtain the relative collection time arrays t(n);

The discrete processing module combines the contrast agent concentration curve C(n) with the relative collection time arrays t(n) to obtain the tissue density time function diagram of each pixel point; after fitting or interpolating the function diagram, re-discretized at the same time interval to obtain the function graph after discrete, then the discrete function graph is the time-corrected tissue density time curve.

Optionally, the discrete function graph includes the discrete time-concentration curve C(n)' described in this disclosure and the arterial input function AIF(n)'.

The present disclosure also provides a system for obtaining CT perfusion imaging parameter maps of brain, including a terminal and a server, wherein the server includes a computer memory, a computer processor, and a computer program stored in the computer memory and executable on the computer processor. The server obtains CT perfusion images from the terminal;

When the computer processor executes the computer program, the method for obtaining brain CT perfusion imaging parameter maps described in the present disclosure is implemented.

The present disclosure also provides a computer-readable storage medium, which stores a computer program, and when the computer program is executed by a computer processor, the method for obtaining brain CT perfusion imaging parameter maps described in the present disclosure is implemented.

The method for obtaining brain CT perfusion imaging parameter maps in the present disclosure has at least the following effects:

After fitting or interpolating the discrete time-concentration curve of each pixel point, re-discretizing at the same time interval, so that the images of different frames of the same image sequence have the same acquisition time, which improves the usability of the time-concentration curve, helps reduce the difficulty of solving problems and improves the accuracy of the solution;

By fitting or interpolating the tissue time-concentration curve and the arterial input function at the same time, and then re-discretizing according to the same time interval, so that the tissue time-concentration curve and the arterial input function have the same starting time and the same time interval, which further reduces the the difficulty of solving problems and improves the accuracy of solving perfusion parameters;

After fitting or interpolating the venous output function, re-discretizing according to the same time interval, so that the images of different frames of the same image sequence have the same acquisition time, which improves the usability of the venous output function.

DETAILED DESCRIPTION

In the prior art, the deconvolution method is currently the most commonly used CT perfusion image processing method. See formula (1): $c(t)=AIF(t)*k(t)$; where C(t) is the tissue time density curve; AIF(t) is the arterial input function; k(t) is the residual function; the specific descriptions of the three are common parameters in the prior art, and are not repeated here. The deconvolution method assumes that the arterial input function AIF(t), the tissue temporal density curve C(t), and the residual function k(t) are related to each other through the convolution model, so through the deconvolution operation, the residual function k(t) can be estimated and related perfusion parameters.

Since the acquisition time of each frame of CT perfusion image is discrete, it is necessary to discretize the above formula to obtain formula (2):

$$c(t) = \int_0^\infty AIF(\tau)k(t_j-\tau)d\tau \approx \Delta t \sum_{i=1}^{N} AIF(t_i)k(t_{j-i+1});$$

where $t_j$ is the jth acquisition time point of the CT perfusion image;

$c(t_j)$ is the tissue density at time $t_j$;

AIF is the arterial input function;

k is the residual function;

N is the acquisition frame number of each layer of perfusion images;

$\Delta t$ is the time interval between two consecutive frames of perfusion images of the same layer.

It can be seen from formula (2) that when the deconvolution operation is performed to solve the residual function k(t), the corresponding moments of the arterial input function AIF(t) and the time-concentration curve c(t) must be consistent.

During the acquisition of CT perfusion images, images at different spatial positions (ie, different layers) of the same image sequence may have different acquisition times due to different image acquisition equipment or acquisition methods. When the global arterial input function is deconvolved, the acquisition time of the time-concentration curve of some layers will be inconsistent with the acquisition time of the global arterial input function, which will lead to the underestimation or overestimation of the delay in the calculation results and reduce the accuracy of the final perfusion parameter maps.

At the same time, in the same image sequence, the acquisition time intervals of images at the same spatial position (ie, the same layer) may also be different. When performing discretized deconvolution calculations, the difference in time interval will increase the difficulty of solving the perfusion parameter maps (using Equation 2 to solve the perfusion parameter maps requires the same time interval). In addition, during the acquisition of CT perfusion images, too large acquisition time interval of the same layer of image will lead to lower time resolution of the residual function k(t) obtained through the deconvolution calculation. The parameter Tmax is the time corresponding to the maximum value of the residual function k(t) and is an important reference index for judging whether the tissue is ischemia. It can be understood that the residual function k(t) is a function of "time-value", and Tmax is the corresponding time coordinate of the maximum value of the residual function k(t). Therefore, using this acquisition interval directly will reduce the accuracy of the resulting perfusion parameter maps.

In order to make the purpose, technical solutions and advantages of the present disclosure clearer, the present disclosure will be described in further detail below with reference to the accompanying drawings and embodiments. It should be understood that the specific embodiments described herein are only used to explain the present disclosure, but not to limit the present disclosure.

Figure 1:
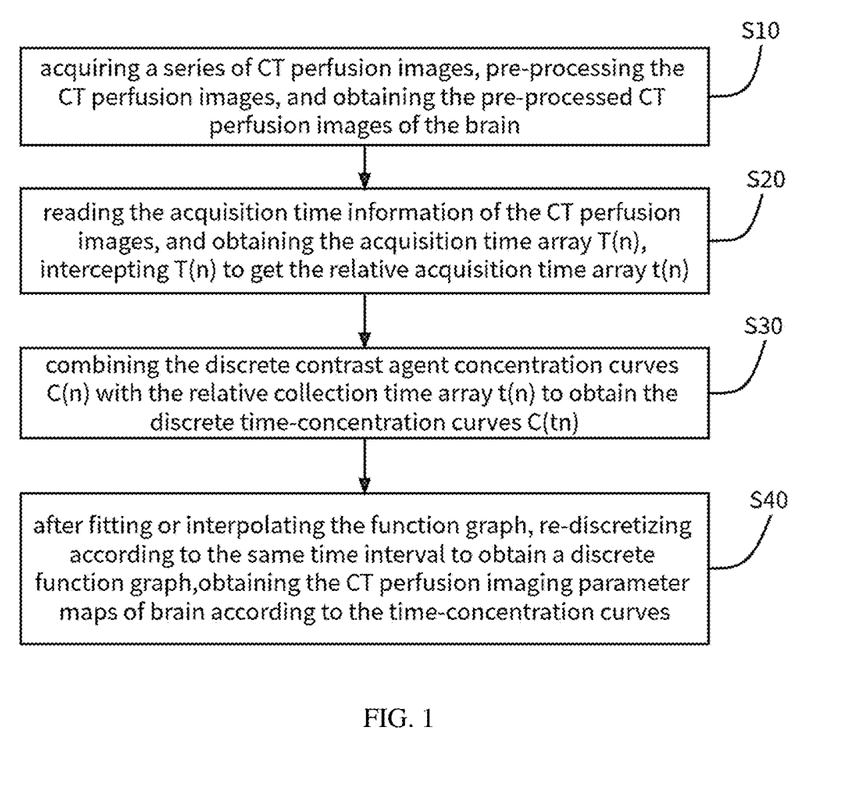
FIG. 1 is a schematic flowchart of a method for obtaining brain CT perfusion imaging parameter maps according to an embodiment of the present disclosure.

In order to solve the above-mentioned technical problems, referring to FIG. 1, an embodiment of the present disclosure provides a method for obtaining brain CT perfusion imaging parameter maps, including:

Step S10, acquiring a series of CT perfusion images, pre-processing the CT perfusion images, and obtaining the pre-processed CT perfusion images of the brain, including the discrete contrast agent concentration curve C(n) of each pixel point in the brain tissue, the global arterial input function AIF(n) and the venous output function VOF(n);

Pre-processing of CT perfusion images includes brain tissue extraction. Specifically, the pre-processing includes motion correction, filtering, skull segmentation to extract brain tissue, and automatic search for arterial and venous points on CT perfusion images.

Step S20, reading the acquisition time information of the CT perfusion images, and obtaining the acquisition time array T(n), where n is the nth time point, T(n) is the physical time of the image acquisition device when the nth image is collected, and T(n) corresponds to the tissue density change curve C(n); intercepting the collection time array T(n) to get the relative acquisition time array t(n);

Step S30, combining the discrete contrast agent concentration curve C(n) with the relative collection time array t(n) to obtain the discrete time-concentration curve $C(t_n)$ of each pixel point in the brain tissue;

Step S40, after fitting or interpolating the function graph, re-discretizing according to the same time interval to obtain a discrete function graph, the discrete function graph is a time-corrected time-concentration curve, obtaining the CT perfusion imaging parameter maps of brain according to the time-concentration curve.

In this embodiment, the brain CT perfusion imaging parameter maps are obtained by processing the tissue time-concentration curve, the arterial input function and the venous output function. The obtained brain CT perfusion imaging parameter maps are obtained by formula 1 according to each function map (tissue time-concentration curve, arterial input function and venous output function), including cerebral blood flow CBF, cerebral blood volume CBV, mean transit time MTT, and Tmax which is the corresponding time coordinate of the maximum value of the residual function k(t), etc., the above parameters are commonly used by those skilled in the art, and will not be explained repeatedly.

In the embodiment of the present disclosure, by fitting or interpolating the tissue time-concentration curve and the arterial input function, the tissue time-concentration curve and the arterial input function in the images of different layers of the same image sequence have the same acquisition time, which is beneficial to improve the accuracy of brain CT perfusion image parameter maps in the subsequent calculation.

It is understandable that during image acquisition of CT perfusion imaging performed at different locations (different layers) of the brain, the physical meaning of n is the same, that is, the nth acquisition time point of the CT perfusion image of this layer. However, since the image acquisition equipment may not be able to complete the acquisition of CT perfusion images of all layers at the same time, the physical time corresponding to the actual nth acquisition time point of different layers of images may be different, so the starting time and time interval of the tissue time-concentration curve, global arterial input function and venous output function of different layers are not necessarily the same. In this embodiment of the present disclosure, after each function graph is fitted or interpolated, re-discretizing according to the same time interval, so that each function graph has the same start time and time interval. In this embodiment, taking any one of the tissue time-concentration curve and the arterial input function as an example, this embodiment improves the reliability of the tissue time-concentration curve or the arterial input function, which helps to reduce the difficulty of solving and improve the accuracy of solving.

Figure 2:
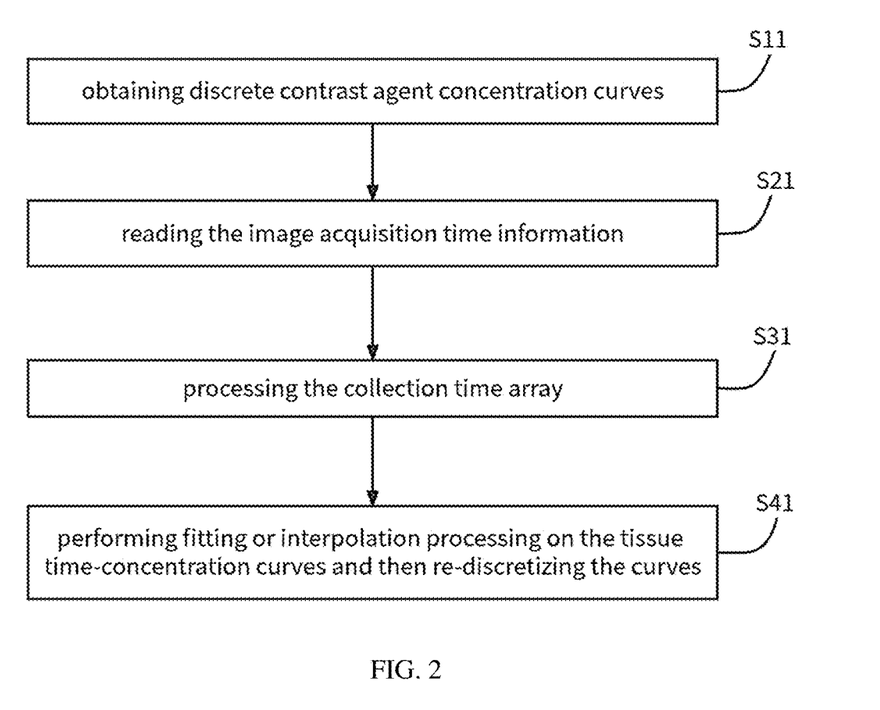
FIG. 2 is a schematic flowchart of a method for obtaining a tissue discrete time-concentration curve C(n)' obtained in a method for obtaining brain CT perfusion imaging parameter maps according to an embodiment of the disclosure.

In another embodiment, referring to FIG. 2, a method for obtaining parametric maps of brain CT perfusion imaging includes:

Step S11, obtaining discrete contrast agent concentration curve, which specifically includes: obtaining CT perfusion images, pre-processing the CT perfusion image, and obtaining discrete contrast agent concentration curve C(n), where n is the nth acquisition time point, and C(n) is the contrast agent concentration in the tissue corresponding to the nth time point;

Step S21, reading the image acquisition time information, which specifically includes: reading the acquisition time information of the CT perfusion images, and obtaining the acquisition time array T(n), where n is the nth time point, and T(n) is the physical time of the image acquisition device when the nth image was collected. T(n) includes $T(c_n)$ corresponding to the discrete contrast agent concentration curve C(n);

It can be understood that the CT perfusion images contain accurate information of the acquisition moment of each frame of the image. When reading the CT perfusion images, the acquisition time of each frame of image is obtained and saved, and finally each pixel point can get an acquisition time array T(n), which corresponds to the discrete contrast agent concentration curve of the pixel point. Likewise, n is the nth acquisition moment of the pixel. All pixels on the same layer of image have the same acquisition time array T(n). It can be seen that T(n) must be a monotonically increasing array.

Step S31, processing the collection time array, specifically including: intercepting the collection time array T(n), obtaining the relative collection time array t(n), and t(n) including $t(c_n)$ corresponding to the discrete contrast agent concentration curve C(n); the discrete contrast agent concentration curve C(n) and the corresponding relative collection time array t(n) are combined to obtain the discrete time-concentration curve $C(t_n)$ of each pixel point;

Step S41, performing fitting or interpolation processing on the tissue time-concentration curve. After fitting or interpolating the discrete tissue time-concentration curve $C(t_n)$, the discrete processing is performed according to the same time interval dt to obtain the discrete tissue time-concentration curve C(n)', obtaining the CT perfusion imaging parameter maps of brain according to the time-concentration curve C(n)'.

In each embodiment of the present disclosure, since the image acquisition time of the CT perfusion image is discrete, the CT perfusion images obtained by pre-processing can be understood as discrete curve, for example, the tissue time-concentration curve $C(t_n)$ is discrete curve. Fitting or interpolating each curve. Specifically, the fitting method includes, but is not limited to, polynomial fitting, curve fitting, and the like. Interpolation method includes but is not limited to Lagrange interpolation, Newton interpolation, Hermite interpolation, spline interpolation, etc.

In another embodiment, the method for obtaining CT perfusion imaging parametric maps of brain further comprises:

Step S12, obtaining the arterial input function, which specifically includes: obtaining CT perfusion images, pre-processing the CT perfusion images, and obtaining the arterial input function AIF(n), where n is the nth acquisition time point;

Step S22, reading the image acquisition time information, which specifically includes: reading the acquisition time information of the CT perfusion images, and obtaining the acquisition time array T(n), where n is the nth time point, T(n) is the physical time of the image acquisition device when the nth image was collected, T(n) also include Ta(n) corresponding to the arterial input function AIF(n);

It can be understood that the CT perfusion image contains accurate information of the acquisition moment of each frame of the image. When reading the CT perfusion images, the acquisition time of each frame of image is obtained and saved, and finally each pixel point can get an acquisition time array T(n), which is related to the arterial input function AIF(n) of the pixel point. Similarly, n is the nth acquisition moment of the pixel. All pixels on the same layer of image have the same acquisition time array T(n).

Step S32, processing the collection time array, specifically including: intercepting the collection time array T(n), obtaining the relative collection time array t(n), and t(n) also including ta (n) corresponding to the arterial input function AIF(n); the discrete arterial input function AIF(n) and the corresponding relative collection time array t(n) are combined to obtain the arterial input function $AIF(t_n)$ of each pixel point.

Step S42, after fitting or interpolating the arterial input function $AIF(t_n)$, re-discretizing at the same time interval to obtain the discrete arterial input function AIF(n)', and obtaining the brain CT perfusion imaging parameter maps according to the arterial input function AIF(n)'.

Figure 3A:
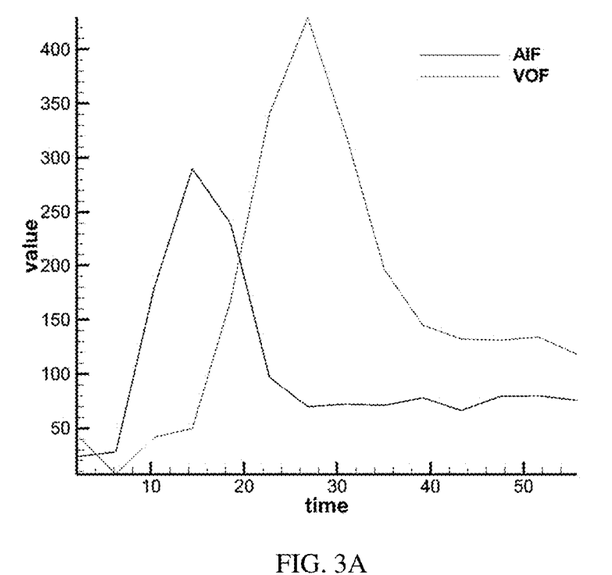
FIGS. 3A-B is a before-and-after comparison diagram of arterial input function (AIF) and venous output function (VOF) obtained by the method described in the present disclosure in different embodiments of the present disclosure.
Figure 3B:
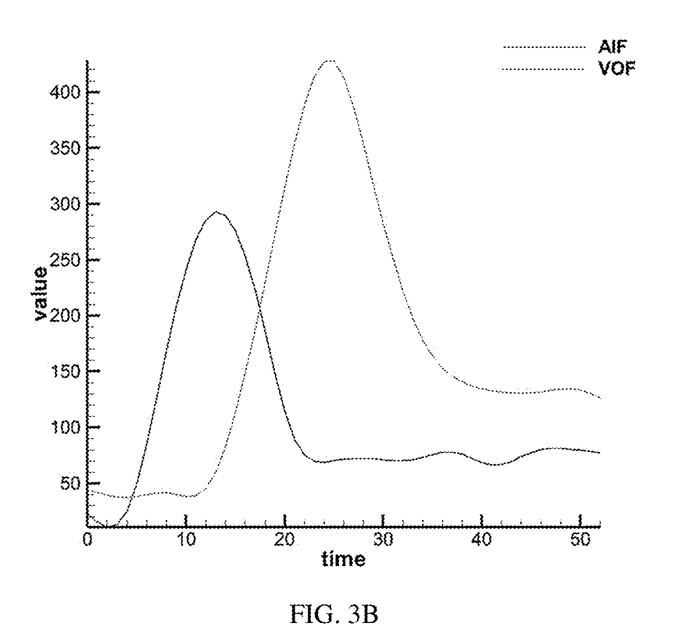

As shown in FIGS. 3A-B, FIG. 3A includes the arterial input function AIF(n) before using the method described in the embodiment of the present disclosure, and FIG. 3B includes the arterial input function AIF(n)' after applying the method described in the embodiment of the present disclosure. As shown in FIGS. 3A-B, the ordinate is the parameter value (value), and the abscissa is different time (time).

In order to realize the disclosure of obtaining parameters, in another embodiment, the method for obtaining brain CT perfusion imaging parameter maps further includes: according to formula (1) c(t)=AIF(t)*k(t), the time-concentration curve C(n)' of each pixel point in brain tissue and the arterial input function AIF(n)' are processed to obtain the discrete residual function k(t)'; where t is the time variable, and k(t) is the residual function. According to the convolution algorithm of the convolution formula (1), it can be understood that the residual function k(t) can be obtained by the operation after deconvolution.

Figure 4A:
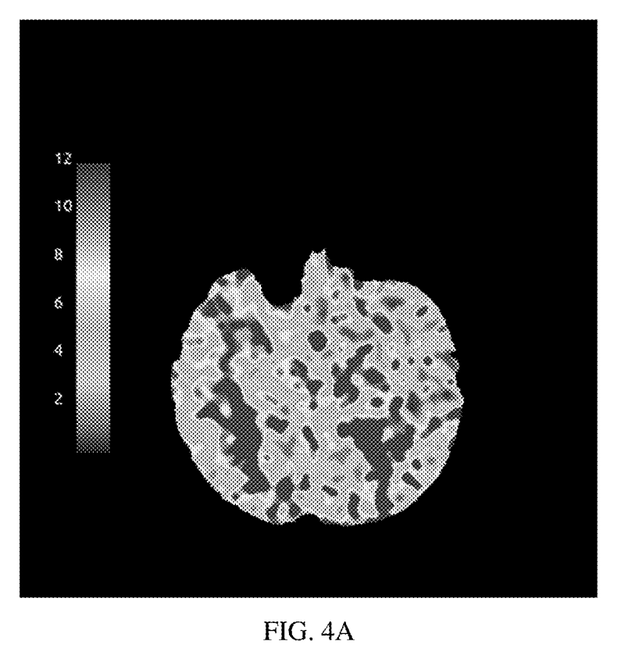
FIG. 4 is a before-and-after comparison diagram of a brain CT perfusion imaging parameter map obtained by the method described in the present disclosure in an embodiment of the present disclosure.
Figure 4B:
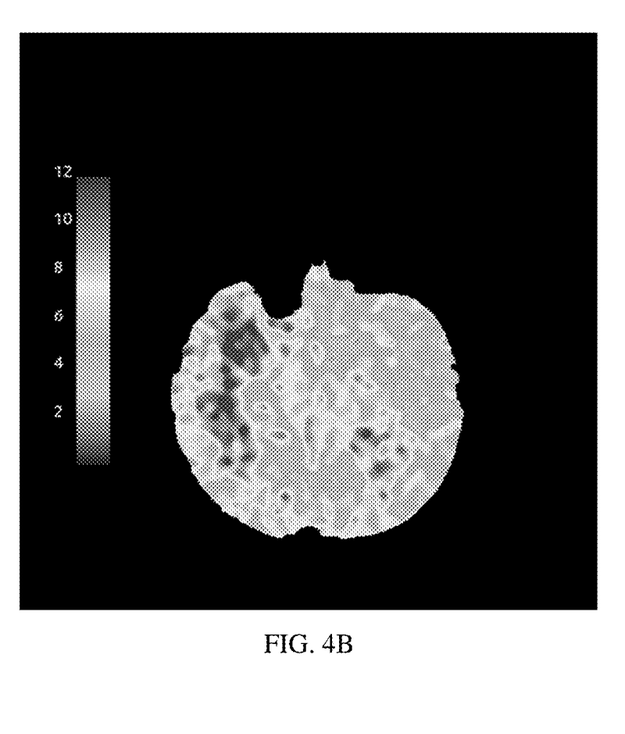

In another embodiment, the discrete time intervals of the discrete time-concentration curve C(n)' and the arterial input function AIF(n)' are the same, and the discrete time-concentration curve C(n)' and the arterial input function AIF(n)' start at the same time. In the embodiment of the present disclosure, by applying time fitting and interpolation processing to the discrete time-concentration curve and the arterial input function AIF at the same time, the tissue time-concentration curve and the arterial input function have the same starting time (Tmin) and the same time interval (dt), so it solves the overestimation or underestimation of delay caused by different starting times in traditional methods, and also solves the increased difficulty of deconvolution algorithms caused by different time intervals. At the same time, reducing the time interval dt (for example, set dt=1) during re-discretization can increase the time resolution of the residual function k(t) calculated by deconvolution, thus improving the accuracy of the final perfusion parameter maps obtained by solution. As shown in FIG. 4A shows the Tmax parameter map obtained before using the methods described in the embodiments of the present disclosure; FIG. 4B shows the Tmax parameter map obtained after adopting the methods described in the various embodiments of the present disclosure. In the figure, it can be seen that the method of obtaining the CT perfusion imaging parameter maps of the brain based on the time fitting and interpolation technology of the present disclosure has significantly improved the result.

In another embodiment, the method for obtaining a brain CT perfusion imaging parameter map further includes:

Step S13, obtaining the venous output function, which specifically includes: obtaining a CT perfusion image, performing pre-processing on the CT perfusion image, and obtaining a venous output function VOF(n), where n is the nth acquisition time point;

Step S23, reading the image acquisition time information, which specifically includes: reading the acquisition time information of the CT perfusion image, and obtaining the acquisition time array T(n), where n is the nth time point, T(n) is the physical time of the image acquisition device when the nth image was collected, T(n) also include Tv(n) corresponding to the arterial input function VOF(n);

Step S33, processing the collection time array, which specifically includes: intercepting the collection time array T(n), obtaining the relative collection time array t(n), and t(n) also including tv(n) corresponding to the venous output function VOF(n); the discrete venous output function VOF(n) and the corresponding relative collection time array t(n) are combined to obtain the venous output function $VOF(t_n)$ of each pixel point.

It can be understood that the CT perfusion image contains accurate information of the acquisition moment of each frame of the image. When reading the CT perfusion image, the acquisition time of each frame of image is obtained and saved, and finally each pixel point can get an acquisition time array T(n), which is related to the venous output function VOF(n) of the pixel point. Similarly, n is the nth acquisition moment of the pixel. All pixel points on the same layer of image have the same acquisition time array T(n).

Step S43, after fitting or interpolating the venous output function $VOF(t_n)$, re-discretizing at the same time interval to obtain the discrete venous output function VOF(n)', and obtaining the brain CT perfusion imaging parameter maps according to the venous output function VOF(n)'.

The discrete time intervals of the discrete time-concentration curve C(n)' and the venous output function VOF(n)' are the same, and the discrete time-concentration curve C(n)' and the venous output function VOF(n)' start at the same time. As shown in FIG. 3A-B, FIG. 3A includes the venous output function VOF(n) before using the method described in the embodiment of the present disclosure, and FIG. 3B includes the venous output function VOF(n)' after applying the method described in the embodiment of the present disclosure.

In this embodiment, after the time correction is performed on the CT perfusion images, the venous output function has the same starting time (Tmin), the same time interval (dt) with other function graphs such as tissue time-concentration curve and arterial input function. This embodiment makes the venous output function VOF(n) and other function graphs have the same starting time and time interval, which improves the accuracy of the final perfusion parameter maps obtained by solution. It solves the overestimation or underestimation of the delay caused by the different starting times in traditional method, and also solves the increased difficulty of the deconvolution algorithms caused by different time intervals. Therefore, the accuracy of the perfusion parameter maps obtained by the final solution is improved.

In order to reveal the acquisition method of the relative collection time array t(n), in another embodiment, the collection time array T(n) is intercepted to obtain the relative collection time array t(n), which specifically includes:

Finding the minimum value Tmin of the acquisition time array T(n) according to the acquisition time array T(n), processing the acquisition time array T(n) according to Tmin, and obtaining the relative collection time arrays t(n) start from the time Tmin.

Specifically, the acquisition time arrays T(n) are converted into the time value measured in seconds, according to the format of the acquisition time in the CT perfusion images; traversing the minimum value t (0) of the acquisition time array of each layer of the CT perfusion images, and finding the minimum value Tmin in all the acquisition time arrays T(n); subtracting Tmin from each element in the collection time array T(n) of each pixel point to obtain the relative collection time array t(n) of each pixel point start from the time Tmin.

Each CT perfusion image is "time-parameter value", which can be understood as a kind of image, and Tmin is a node of the time axis. In different embodiments, the Tmin values used in each CT perfusion images are the same, so as to ensure that each CT perfusion image has the same start time.

For example, the acquisition time array of the first layer of images is T1(*n*), and the image of this layer is collected from time T1(0), then relative to time Tmin, it starts from time t1(0)=T1(0)−Tmin; the acquisition time array of the i-th layer image is Ti(n), and the image layer of this layer starts to be collected from the time of Ti(0), then relative to the time of Tmin, it starts from time ti(0)=Ti(0)−Tmin. Corresponding processing is also performed on the acquisition time array T(n) corresponding to the global arterial input function AIF(n) and the venous output function VOF (n). Therefore, after processing, the elements in the relative collection time array t(n) of all pixel points are the time relative to Tmin.

In conclusion, the present disclosure optimizes the method for obtaining the CT perfusion imaging parameter maps of brain through time fitting and discrete technology, aiming to solve the above three problems, improve the accuracy of the perfusion parametric map solved by the deconvolution method, and reduce the difficulty. The main implementation process of this method is as follows: First, obtaining the pre-processed contrast agent concentration curve C(n) of each pixel point in the brain tissue, the global arterial input function AIF(n) and the venous output function VOF(n), where n is the nth acquisition time point; secondly, reading the acquisition time information of the CT perfusion image, and obtaining the acquisition time array T(n) of each pixel point; thirdly, processing the acquisition time array to obtain the new relative acquisition of each pixel point relative to the same time time array t(n); finally, combining each function or curve with its corresponding relative acquisition time array t(n), performing fitting or interpolation processing on it, and then re-discretizing the curve. Taking the discrete contrast agent concentration curve C(n) as an example, combining the discrete contrast agent concentration curve C(n) with its corresponding relative acquisition time array t(n) to obtain the discrete time-concentration curve $C(t_n)$ on the pixel point. The time-concentration curve are re-discretized after fitting or interpolation processing, and the new tissue time-concentration curve C(n)' with the same starting time and the same time interval are obtained.

It should be understood that although the steps in the flowcharts of FIGS. 1-2 are shown in sequence according to the arrows, these steps are not necessarily executed in the sequence shown by the arrows. Unless explicitly stated herein, the execution of these steps is not strictly limited to the order, and these steps may be performed in other orders. Moreover, at least a part of the steps in FIGS. 1-2 may include multiple sub-steps or multiple stages. These sub-steps or stages are not necessarily executed at the same time, but may be executed at different times. These sub-steps or stages are not necessarily completed at the same time. The order of execution of the steps is not necessarily sequential, but may be performed alternately or alternately with other steps or at least a part of sub-steps or stages of other steps.

Figure 5:
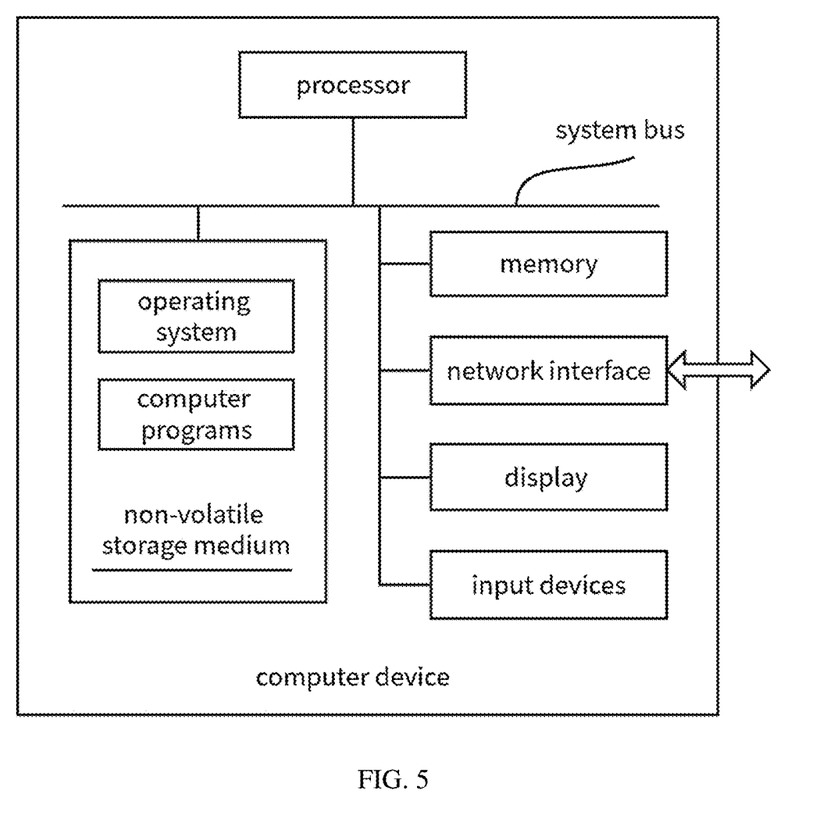
FIG. 5 is a structural block diagram of an apparatus for obtaining brain CT perfusion imaging parameter maps according to an embodiment of the present disclosure.

In one embodiment, as shown in FIG. 5, a method for obtaining CT perfusion imaging parameter maps of brain is provided. It includes: a pre-processing module, a time processing module and a discrete processing module, wherein:

The pre-processing module acquires CT perfusion images, pre-processes the CT perfusion images, and acquires pre-processed brain CT perfusion images, tissue contrast agent concentration curve C(n), global arterial input function AIF(n) and venous output function VOF(n);

The time processing module reads the acquisition time information of the CT perfusion images, and acquires the acquisition time array T(n), where n is the nth time point, T(n) is the physical time of the image acquisition device when the nth image was collected, T(n) corresponds to the discrete contrast agent concentration curve C(n); intercepts the acquisition time array T(n) to obtain the relative acquisition time array t(n);

The discrete processing module combines the contrast agent concentration curve C(n) with the relative acquisition time array t(n), obtains the discrete time-concentration curve of each pixel point; after fitting or interpolating the function, re-discretizing it at same time interval to acquire the discrete function. The discrete function graph is the time-concentration curve corrected with respect to time.

Specific qualifications of the device for obtaining CT perfusion imaging parameter maps of the brain can be found above for the qualification of methods for obtaining CT perfusion imaging parameter maps of the brain, which will be omitted here. Modules in the device for acquiring perfusion imaging parametric maps described above can be fully or partially implemented by software, hardware, or a combination thereof. Each of the above modules can be embedded in or independent of the processor in the computer in hardware form, or stored in the memory in the computer device in software form, so that the processor can call and execute the operations corresponding to each module above.

In one embodiment, a computer device is provided. It may be a terminal, and its internal structure diagram can be shown in FIG. 5. This computer device includes a processor, memory, network interface, display and input devices, which are all connected by the system bus. Wherein, the processor provides computing and control capabilities. The memory of the computer device includes a non-volatile storage medium and an internal memory. The non-volatile storage medium stores an operating system and computer programs. The internal memory provides an running environment for the operating system and computer programs stored in the non-volatile storage medium. The network interface of the computer device is used to communicate with external terminals through a network connection. The computer program, when executed by the processor, implements a method for obtaining CT perfusion imaging parameter maps of the brain. The display screen of the computer equipment may be a liquid crystal screen or electronic ink display screen, the input device of the computer equipment can be a touch layer on the display screen, or buttons, a trackball, a touchpad set on the shell of the computer equipment, or it can be the external connected keyboard, trackpad, or mouse, etc.

One of ordinary skill in the art to which this invention belongs can understand that the structure in FIG. 5 only shows part of the structure related to disclosure, which does not constitute a limitation on the computer equipment to which the method of this disclosure is applied. A particular computer device may include more or fewer components than those shown in the figures, or has certain components combined, or has a different arrangement of components.

In one embodiment, a system for acquiring CT perfusion imaging parameter maps of the brain is provided, including a terminal and a server. The server includes a computer memory, a computer processor, and the computer program stored in the memory which is executable on the computer processor. The server obtains the CT perfusion images from the terminal. When the computer processor executes the computer program, the following steps are implemented:

Step S11, acquiring contrast agent concentration curve, which specifically includes: acquiring CT perfusion images, pre-processing the images to obtain the discrete tissue contrast agent concentration curve C(n), where n is the nth acquisition time point, C(n) is the contrast agent concentration in the tissue corresponding to the nth time point;

Step S21, reading image acquisition time information, which specifically includes: reading the acquisition time information of the CT perfusion images, obtaining the acquisition time array T(n), where n is the nth time point, and T(n) is the physical time of the image acquisition device when the nth image was collected. T(n) includes Tc (n) corresponding to the discrete contrast agent concentration curve C(n);

Step S31, processing the acquisition time array, specifically includes: intercepting the acquisition time array T(n), obtaining the relative acquisition time array t(n), t(n) including $C(t_n)$ corresponding to the discrete contrast agent concentration curve C(n); combining the contrast agent concentration curve C(n) with the corresponding relative acquisition time array t(n) to obtain the discrete time-concentration curve $C(t_n)$ of each pixel point;

Step S41, performing fitting or interpolation processing on the time-concentration curve After the discrete time-concentration curve $C(t_n)$ is fitted or interpolated, re-discretizing it at same time interval dt to obtain the discrete time-concentration curve C(n)' of each pixel point, obtaining the parametric maps of brain CT perfusion imaging according to the time-concentration curve C(n)'.

In one embodiment, a computer-readable storage medium having a computer program stored there is provided. When the processor executes the program, it implements the following steps:

Step S11, acquiring contrast agent concentration curve, which specifically includes: acquiring CT perfusion images, pre-processing the images to obtain the discrete tissue contrast agent concentration curve C(n), where n is the nth acquisition time point, C(n) is the contrast agent concentration in the tissue corresponding to the nth time point;

Step S21, reading image acquisition time information, which specifically includes: reading the acquisition time information of the CT perfusion images, obtaining the acquisition time array T(n), where n is the nth time point, and T(n) is the physical time of the image acquisition device when the nth image was collected. T(n) includes Tc (n) corresponding to the discrete contrast agent concentration curve C(n);

Step S31, processing the acquisition time array, specifically includes: intercepting the acquisition time array T(n), obtaining the relative acquisition time array t(n), t(n) including $C(t_n)$ corresponding to the discrete contrast agent concentration curve C(n); combining the contrast agent concentration curve C(n) with the corresponding relative acquisition time array t(n) to obtain the discrete time-concentration curve $C(t_n)$ of each pixel point;

Step S41, performing fitting or interpolation processing on the time-concentration curve After the discrete time-concentration curve $C(t_n)$ is fitted or interpolated, re-discretizing it at same time interval dt to obtain the discrete time-concentration curve C(n)' of each pixel point.

In one embodiment, the processor further implements the following steps when executing the program:

Step S12, acquiring the arterial input function, which specifically includes: acquiring CT perfusion images, pre-processing the images to obtain the arterial input function AIF(n), where n is the nth acquisition time point;

step S22, reading the image acquisition time information, which specifically includes: reading the acquisition time information of the CT perfusion images, obtaining the acquisition time array T(n), where n is the nth time point, and T(n) is the physical time of the image acquisition device when the nth image was collected. T(n) also includes Ta(n) corresponding to the arterial input function AIF(n);

step S32, processing the acquisition time array, which specifically includes: intercepting the acquisition time array T(n) to obtain the relative acquisition time array t(n), t(n) also including ta (n) corresponding to the arterial input function AIF(n); combining the arterial input function AIF(n) with the corresponding relative acquisition time array t(n) to obtain the arterial input function $AIF(t_n)$;

Step S42, after fitting or interpolating the arterial input function $AIF(t_n)$, re-discretizing it at same time interval to obtain the discrete arterial input function AIF(n)', obtaining the parametric maps of brain CT perfusion imaging according to the arterial input function AIF(n)'.

In one embodiment, the computer processor further implements the following steps when executing the program:

Step S13, acquiring the venous output function, which specifically includes: acquiring CT perfusion images, pre-processing the images to obtain the venous output function VOF(n), where n is the nth acquisition time point;

Step S23, reading the image acquisition time information, which specifically includes: reading the acquisition time information of the CT perfusion images, obtaining the acquisition time array T(n), where n is the nth time point, and T(n) is the physical time of the image acquisition device when the nth image was collected. T(n) also includes Tv(n) corresponding to the venous output function VOF(n);

Step S33, processing the acquisition time array, which specifically includes: intercepting the acquisition time array T(n) to obtain the relative acquisition time array t(n), t(n) also includes tv(n) corresponding to the venous output function VOF(n); combining the venous output function VOF(n) with the corresponding relative acquisition time array t(n) to obtain the venous output function VOF($t_n$);

Step S43, after fitting or interpolating the venous output function VOF($t_n$), re-discretizing it at same time interval to obtain the discrete venous output function VOF(n)', obtaining CT perfusion imaging parameter maps of the brain according to the venous output function VOF(n)'. The discrete time interval of the output function VOF(n)' is the same as the tissue time-concentration curve C(n)' and their starting times are the same too. As shown in FIG. 3, FIG. 3A shows the venous output function VOF(n) before using the method described in this specification, while FIG. 3B shows the VOF(n)' after using the method.

In one embodiment, a computer-readable storage medium having a computer program stored there is provided. The computer program, when executed by a processor, implements the following steps:

Step S11, acquiring contrast agent concentration curve, which specifically includes: acquiring CT perfusion images, pre-processing the images to obtain the discrete tissue contrast agent concentration curve C(n), where n is the nth acquisition time point, C(n) is the contrast agent concentration in the tissue corresponding to the nth time point;

Step S21, reading image acquisition time information, which specifically includes: reading the acquisition time information of the CT perfusion images, obtaining the acquisition time array T(n), where n is the nth time point, and T(n) is the physical time of the image acquisition device when the nth image was collected. T(n) includes Tc (n) corresponding to the discrete contrast agent concentration curve C(n);

Step S31, processing the acquisition time array, specifically includes: intercepting the acquisition time array T(n), obtaining the relative acquisition time array t(n), t(n) including C($t_n$) corresponding to the discrete contrast agent concentration curve C(n); combining the contrast agent concentration curve C(n) with the corresponding relative acquisition time array t(n) to obtain the discrete time-concentration curve C($t_n$) of each pixel point;

Step S41, performing fitting or interpolation processing on the time-concentration curve After the discrete time-concentration curve C($t_n$) is fitted or interpolated, re-discretizing it at same time interval dt to obtain the discrete time-concentration curve C(n)' of each pixel point.

In one embodiment, the computer program further implements the following steps when executed by the processor:

Step S12, acquiring the arterial input function, which specifically includes: acquiring CT perfusion images, pre-processing the images to obtain the arterial input function AIF(n), where n is the nth acquisition time point;

step S22, reading the image acquisition time information, which specifically includes: reading the acquisition time information of the CT perfusion images, obtaining the acquisition time array T(n), where n is the nth time point, and T(n) is the physical time of the image acquisition device when the nth image was collected. T(n) also includes Ta(n) corresponding to the arterial input function AIF(n);

step S32, processing the acquisition time array, which specifically includes: intercepting the acquisition time array T(n) to obtain the relative acquisition time array t(n), t(n) also including ta (n) corresponding to the arterial input function AIF(n); combining the arterial input function AIF(n) with the corresponding relative acquisition time array t(n) to obtain the arterial input function AIF($t_n$);

Step S42, after fitting or interpolating the arterial input function AIF($t_n$), re-discretizing it at same time interval to obtain the discrete arterial input function AIF(n)', obtaining the parametric maps of brain CT perfusion imaging according to the arterial input function AIF(n)'.

In one embodiment, the computer program further implements the following steps when executed by the processor:

Step S13, acquiring the venous output function, which specifically includes: acquiring CT perfusion images, pre-processing the images to obtain the venous output function VOF(n), where n is the nth acquisition time point;

Step S23, reading the image acquisition time information, which specifically includes: reading the acquisition time information of the CT perfusion images, obtaining the acquisition time array T(n), where n is the nth time point, and T(n) is the physical time of the image acquisition device when the nth image was collected. T(n) also includes Tv(n) corresponding to the venous output function VOF(n);

Step S33, processing the acquisition time array, which specifically includes: intercepting the acquisition time array T(n) to obtain the relative acquisition time array t(n), t(n) also includes tv(n) corresponding to the venous output function VOF(n); combining the venous output function VOF(n) with the corresponding relative acquisition time array t(n) to obtain the venous output function VOF($t_n$);

Step S43, after fitting or interpolating the venous output function VOF($t_n$), re-discretizing it at same time interval to obtain the discrete venous output function VOF(n)', obtaining CT perfusion imaging parameter maps of the brain according to the venous output function VOF(n)'. The discrete time interval of the output function VOF(n)' is the same as the tissue time-concentration curve C(n)' and their starting times are the same too. As shown in FIGS. 3A-B, FIG. 3A shows the venous output function VOF(n) before using the method described in this specification, while FIG. 3B shows the VOF(n)' after using the method.

One of ordinary skill in the art to which this invention belongs can understand that all or at least part of the methods described in the above embodiments can be realized by instructing the relevant hardware through a computer program. The computer program can be stored in a non-volatile computer-readable storage medium. The computer program, when executed, may implement the steps of the above-mentioned embodiments. All references to memory, storage, database or other medium in above embodiments provided in this disclosure may include non-volatile and/or volatile memory. Non-volatile memory includes read only memory (ROM), programmable ROM (PROM), electrically programmable ROM (EPROM), electrically erasable programmable ROM (EEPROM), or Flash. Volatile memory includes random access memory (RAM) or external cache memory. As a description rather than a limitation, RAM is available in many forms such as static RAM (SRAM), dynamic RAM (DRAM), synchronous DRAM (SDRAM), double data rate SDRAM (DDRSDRAM), enhanced SDRAM (ESDRAM), synchlink DRAM (SLDRAM), memory Bus (Rambus) direct RAM (RDRAM), direct memory bus dynamic RAM (DRDRAM), and memory bus dynamic RAM (RDRAM) etc.

The technical features of the above embodiments can be combined arbitrarily. For the sake of brevity, not all possible combinations of the various technical features in the embodiments are described. However, as long as there is no contradiction, it should be regarded within the scope of the description in this specification. When technical features in different embodiments are embodied in a same drawing, it can be regarded that the drawing also discloses a combination of various embodiments involved.

The above embodiments only express several embodiments of the present disclosure, and the descriptions thereof are more specific and detailed. However, it should not be construed as a limitation on the scope of the invention patent. It should be pointed out that for one with ordinary skill in the art, several deformations and modifications can also be made on the premise of not departing from the concept of the present disclosure. Further, these all belong to the protection scope of the present disclosure. Therefore, the scope of protection of the patent applied should be subject to the appended claims.

The invention claimed is:

1. A method for obtaining the CT perfusion imaging parameter maps of brain, comprising:
    obtaining CT perfusion images, performing pre-processing on the CT perfusion images, and obtaining a discrete contrast agent concentration curve C(n) of each pixel point in the brain tissue, where n is the nth time point, and each element in C(n) is contrast agent concentration in the tissue corresponding to one time point;
    reading acquisition time information of the CT perfusion images, and obtaining an acquisition time arrays T(n), where n is the nth time point, T(n) is physical time of image acquisition device when the nth image was collected, T(n) include Tc (n) corresponding to discrete contrast agent concentration curve C(n), and Tc (n) is a subset of T(n);
    the acquisition time array T(n) are converted into the time value measured in seconds, according to the format of the acquisition time in the CT perfusion images; and finding the minimum value Tmin in all the acquisition time array T(n); Subtracting Tmin from each element in the acquisition time array T(n) of each pixel point to obtain the relative acquisition time array t(n) of each pixel point start from the time Tmin, where t(n) include tc(n) corresponding to discrete contrast agent concentration curve C(n), and tc(n) is a subset of t(n);
    combining the discrete contrast agent concentration curve C(n) with the corresponding relative acquisition time array t(n) to obtain the discrete time-concentration curve $C(t_n)$ of each pixel point in the brain tissue;
    after fitting or interpolating the discrete time-concentration curve $C(t_n)$ of each pixel point, re-discretizing at same time interval to obtain the discrete time-concentration curve C(n)' of each pixel point in brain tissue, obtaining the CT perfusion imaging parameter maps of brain according to the time-concentration curve C(n)'.

2. The method for obtaining the CT perfusion imaging parameter maps of brain according to claim 1, further comprising:
    obtaining CT perfusion images, performing pre-processing on the CT perfusion images, and obtaining an arterial input function AIF(n), where n is the nth acquisition time point;
    reading the acquisition time information of the CT perfusion images, and obtain the acquisition time array T(n), where n is the nth time point, T(n) is the physical time of the image acquisition device when the nth image was collected, T(n) also include Ta(n) corresponding to the arterial input function AIF(n);
    intercepting the acquisition time array T(n) to obtain the relative acquisition time array t(n), t(n) also include ta (n) corresponding to the arterial input function AIF(n);
    combining the arterial input function AIF(n) with the corresponding relative acquisition time array t(n) to obtain the arterial input function $AIF(t_n)$;
    after fitting or interpolating the arterial input function $AIF(t_n)$, re-discretizing at the same time interval to obtain the discrete arterial input function AIF(n)', and obtaining the CT perfusion imaging parameter maps of brain according to the arterial input function AIF(n)'.

3. The method for obtaining the CT perfusion imaging parameter maps of brain according to claim 2, further comprising:
    according to the formula c(t)=AIF(t)*k(t), the time-concentration curve C(n)' of each pixel point in brain tissue and the arterial input function AIF(n)' are processed to obtain the discrete residual function k(t)';
    where t is the time and k(t) is the residual function.

4. The system for obtaining CT perfusion imaging parameter maps of brain includes the terminal and the server, wherein the server comprises the computer memory, the computer processor, and the computer program stored in the computer memory and executable on the computer processor, wherein the server obtains CT perfusion images from the terminal; when the computer processor executes the computer program, the method for obtaining brain CT perfusion imaging parameter maps according to claim 3 is implemented.

5. The method for obtaining the CT perfusion imaging parameter maps of brain according to claim 2, wherein, the discrete time intervals of the discrete time-concentration curve C(n)' and the arterial input function AIF(n)' are the same, and the discrete time-concentration curve C(n)' and the arterial input function AIF(n)' start at the same time.

6. The system for obtaining CT perfusion imaging parameter maps of brain includes the terminal and the server, wherein the server comprises the computer memory, the computer processor, and the computer program stored in the computer memory and executable on the computer processor, wherein the server obtains CT perfusion images from the terminal; when the computer processor executes the computer program, the method for obtaining brain CT perfusion imaging parameter maps according to claim 5 is implemented.

7. The system for obtaining CT perfusion imaging parameter maps of brain includes the terminal and the server, wherein the server comprises the computer memory, the computer processor, and the computer program stored in the computer memory and executable on the computer processor, wherein the server obtains CT perfusion images from the terminal; when the computer processor executes the computer program, the method for obtaining brain CT perfusion imaging parameter maps according to claim 2 is implemented.

8. The method for obtaining the CT perfusion imaging parameter maps of brain according to claim 1, wherein, the pre-processing comprising: performing motion correction, filtering, segmenting the skull and extract brain area, finding arterial and venous points automatically on the CT perfusion image.

9. The system for obtaining CT perfusion imaging parameter maps of brain includes the terminal and the server, wherein the server comprises the computer memory, the computer processor, and the computer program stored in the computer memory and executable on the computer processor, wherein the server obtains CT perfusion images from the terminal; when the computer processor executes the computer program, the method for obtaining brain CT perfusion imaging parameter maps according to claim 8 is implemented.

10. The system for obtaining CT perfusion imaging parameter maps of brain includes the terminal and the server, wherein the server comprises the computer memory, the computer processor, and the computer program stored in the computer memory and executable on the computer processor, wherein the server obtains CT perfusion images from the terminal; when the computer processor executes the computer program, the method for obtaining brain CT perfusion imaging parameter maps according to claim 5 is implemented.

11. The method for obtaining the CT perfusion imaging parameter maps of brain according to claim 1, further comprising:
  acquiring CT perfusion images, performing pre-processing on the CT perfusion images, and obtaining a venous output function VOF(n), where n is the nth acquisition time point;
  reading the acquisition time information of the CT perfusion images, and obtaining the acquisition time array T(n), where n is the nth time point, T(n) is the physical time of the image acquisition device when the nth image was collected, T(n) also include Tv(n) corresponding to the venous output function VOF(n);
  Intercepting the acquisition time array T(n) to obtain the relative acquisition time array t(n), t(n) also include tv(n) corresponding to the venous output function VOF(n);
  combining the venous output function VOF(n) with the corresponding relative acquisition time array t(n) to obtain the venous output function $VOF(t_n)$;
  after fitting or interpolating the venous output function $VOF(t_n)$, re-discretizing at the same time interval to obtain the discrete venous output function VOF(n)', and obtaining the CT perfusion imaging parameter maps of brain according to the venous output function VOF(n)';
  the discrete time intervals of the discrete time-concentration curve C(n)' and the venous output function VOF(n)' are the same, and the discrete time-concentration curve C(n)' and the venous output function VOF(n)' start at the same time.

12. The system for obtaining CT perfusion imaging parameter maps of brain includes the terminal and the server, wherein the server comprises the computer memory, the computer processor, and the computer program stored in the computer memory and executable on the computer processor, wherein the server obtains CT perfusion images from the terminal; when the computer processor executes the computer program, the method for obtaining brain CT perfusion imaging parameter maps according to claim 11 is implemented.

13. The system for obtaining CT perfusion imaging parameter maps of brain includes a terminal and a server, wherein the server comprises a computer memory, a computer processor, and a computer program stored in the computer memory and executable on the computer processor, wherein the server obtains CT perfusion images from the terminal; when the computer processor executes the computer program, the method for obtaining brain CT perfusion imaging parameter maps according to claim 1 is implemented.

14. A computer-readable storage medium, which stores a computer program, wherein, when the computer program is executed by a computer processor, the method for obtaining brain CT perfusion imaging parameter maps according to claim 1 is implemented.

15. The computer-readable storage medium of claim 14, wherein obtaining CT perfusion images, performing pre-processing on the CT perfusion images, and obtaining the arterial input function AIF(n), where n is the nth acquisition time point;
  reading the acquisition time information of the CT perfusion images, and obtain the acquisition time array T(n), where n is the nth time point, T(n) is the physical time of the image acquisition device when the nth image was collected, T(n) also include Ta(n) corresponding to the arterial input function AIF(n);
  intercepting the acquisition time array T(n) to obtain the relative acquisition time array t(n), wherein t(n) also includes ta (n) corresponding to the arterial input function AIF(n);
  combining the arterial input function AIF(n) with the corresponding relative acquisition time array t(n) to obtain the arterial input function $AIF(t_n)$; and
  after fitting or interpolating the arterial input function $AIF(t_n)$, re-discretizing at the same time interval to obtain the discrete arterial input function AIF(n)', and obtaining the CT perfusion imaging parameter maps of brain according to the arterial input function AIF(n)'.

16. The computer-readable storage medium of claim 14, further comprising:
  according to the formula c(t)=AIF(t)*k(t), the time-concentration curve C(n)' of each pixel point in brain tissue and the arterial input function AIF(n)' are processed to obtain the discrete residual function k(t)'; and
  where t is the time and k(t) is the residual function.

17. The computer-readable storage medium of claim 14, wherein, the pre-processing comprising: performing motion correction, filtering, segmenting the skull and extract brain area, finding arterial and venous points automatically on the CT perfusion image.

18. The computer-readable storage medium of claim 14, wherein, the intercepting the acquisition time array T(n) to obtain the relative acquisition time array t(n), which specifically includes:
  the acquisition time array T(n) are converted into the time value measured in seconds, according to the format of the acquisition time in the CT perfusion images;
  traversing the minimum value t(0) of the acquisition time array of each layer of the CT perfusion images, and finding the minimum value Tmin in all the acquisition time array T(n); and
  subtracting Tmin from each element in the acquisition time array T(n) of each pixel point to obtain the relative acquisition time array t(n) of each pixel point start from the time Tmin.

19. The device for obtaining the CT perfusion imaging parameter map of brain, comprising:
  a pre-processing module acquires the CT perfusion images, performs pre-processing on the CT perfusion images, and obtains pre-processed CT perfusion images of brain, including a discrete contrast agent concentration curve C(n) of each pixel point in brain tissue and a global arterial input function AIF(n) and a venous output function VOF(n);

a time processing module reads acquisition time information of the CT perfusion images, and obtains an acquisition time arrays T(n), where n is the nth time point, and T(n) is the physical time of image acquisition device when the nth image is collected, T(n) corresponds to the contrast agent concentration curve C(n); intercepts the acquisition time arrays T(n) to obtain a relative acquisition time arrays t(n);

a discrete processing module combines the contrast agent concentration curve C(n) with the relative acquisition time array t(n) to obtain the tissue density time function diagram of each pixel point; after fitting or interpolating the function diagram, re-discretizing at the same time interval to obtain the function graph after discretized, then the discrete function graph is the time-corrected tissue density time curve.

* * * * *